(12) United States Patent
Steffen

(10) Patent No.: US 8,728,126 B2
(45) Date of Patent: May 20, 2014

(54) BONE FIXATION SYSTEM AND METHOD

(76) Inventor: Dennis L. Steffen, Tavernier, FL (US)

( * ) Notice: Subject to any disclaimer, the term of this patent is extended or adjusted under 35 U.S.C. 154(b) by 298 days.

(21) Appl. No.: 12/706,036

(22) Filed: Feb. 16, 2010

(65) Prior Publication Data
US 2010/0145339 A1    Jun. 10, 2010

Related U.S. Application Data

(63) Continuation-in-part of application No. 12/398,882, filed on Mar. 5, 2009.

(60) Provisional application No. 61/035,138, filed on Mar. 10, 2008.

(51) Int. Cl.
*A61B 17/80*    (2006.01)

(52) U.S. Cl.
USPC ........................................ 606/282

(58) Field of Classification Search
USPC ........................................ 606/280
See application file for complete search history.

(56) References Cited

U.S. PATENT DOCUMENTS

| | | | | |
|---|---|---|---|---|
| 5,364,399 | A * | 11/1994 | Lowery et al. | 606/295 |
| 5,681,311 | A * | 10/1997 | Foley et al. | 606/283 |
| 6,669,701 | B2 * | 12/2003 | Steiner et al. | 606/282 |
| 7,354,441 | B2 | 4/2008 | Frigg | |
| 8,100,953 | B2 * | 1/2012 | White et al. | 606/280 |
| 2005/0004574 | A1 * | 1/2005 | Muckter | 606/69 |
| 2006/0235400 | A1 * | 10/2006 | Schneider | 606/69 |
| 2006/0264946 | A1 * | 11/2006 | Young | 606/69 |
| 2008/0140130 | A1 * | 6/2008 | Chan et al. | 606/280 |
| 2009/0228010 | A1 * | 9/2009 | Gonzalez-Hernandez et al. | 606/70 |

FOREIGN PATENT DOCUMENTS

DE    43 43 117    6/1995

OTHER PUBLICATIONS

Lakatos et al. "General Principles of Internal Fixation" published on eMedicine.com, retrieved from http://emedicine.medscape.com/article/1269987-print on Aug. 12, 2009, updated May 29, 2007, 43 pages.
"Zimmer® Universal Locking System", The Journal of Bone and Joint Surgery, vol. 89-A, No. 7, Jul. 2007, 1 page.
"MIS Technique", published by Zimmer®, 1 page (undated).
Locking Compression Plate (LCP), 1 page (undated).

* cited by examiner

*Primary Examiner* — Matthew Lawson
*Assistant Examiner* — Zade Coley

(57) ABSTRACT

A bone fixation system includes a bone plate having bi-directional combination holes extending therethrough, each hole being composed of a pair of domains and an interconnect which prevents the holes from overlapping. Each of the holes is configured and dimensioned to receive a set of full head bone screws adapted to be anchored into a bone or fragments thereof. The system also includes a pair of bone screws received in at least one of the combination holes, each bone screw having a shaft and a full head and being oriented in non-parallel directions. Various bone plate and screw embodiments are disclosed as is a method for fixating a bone fracture using the fixation system.

19 Claims, 4 Drawing Sheets

BONE FIXATION SYSTEM AND METHOD

CROSS-REFERENCE TO RELATED APPLICATIONS

This application is a continuation-in-part of U.S. Ser. No. 12/398,882, filed Mar. 5, 2009, which claims the benefit of Provisional Application Ser. No. 61/035,138, filed Mar. 10, 2008, the entire contents of which are hereby incorporated by reference herein.

BACKGROUND OF THE INVENTION

1. Field of the Invention

The present invention relates to a bone fixation system and method for fracture fixation of bone.

Conventional bone fixation systems include a bone fracture fixation plate for placement on a bone so as to bridge a fracture therein and a set of screws inserted through the plate into the bone. The system works by drawing the fracture fragments to the plate, and if the plate is designed with "compression" holes, the fracture fragments can be made to compress against each other to promote primary bone healing. However, the angular relationship between the plate and screws is not fixed and can change postoperatively. As such, this can lead to misalignment and poor clinical results.

2. Prior Art

One method of securing the screws to a bone plate involves the use of so-called "locking screws." A locking screw has a male thread on an outer surface of its head that interfaces With a female thread on the plate to lock the screw to the plate. Bone plates having threaded holes for accommodating locking screws are known. For example, German Patent Application No. 43 43 117 discloses a bone plate with threaded holes for locking screws. As the relationship between the locking screws and the plate is fixed, locking screws provide a high resistance to shear or torsion forces. However, locking screws have a limited capability to Compress bone fragments.

Another approach to construction of a bone plate involves use of "combination holes." Combination holes in the bone plates have a domain for non-locking screws and another domain for locking screws. Here, the locking screws can only be applied in a direction perpendicular to the plate; (see, e.g., U.S. Pat. No. 6,469,701 and U.S. Pat. No. 7,354,441). However, only a one locking or a non-locking screw can be applied in each of these "combination" holes along the bone plate.

Another bone plate hole configuration involves a "figure-eight" hole; see, e.g., Universal Locking System available from Zimmer Holdings, Inc. (Warsaw, Ind.) and 1 Bone and Joint Surgery, 89(7) 2007. Here, a figure-eight-type hole in the bone plate has two parallel threaded domains. A locking screw can be mated to one domain of the hole or to the other domain of the same hole. In each case, the locking screw can be applied only perpendicular to the bone plate. Further, only one screw can he received in each of these figure-eight-type holes along the plate.

In yet another approach, the bone plate has individual locking holes for mating individual locking screws; see, e.g., MIS Technique available from Zimmer Holdings, Inc. (Warsaw, Ind.) Here, the individual holes are oriented alternating in one direction and in another direction (in the plane transverse to the longitudinal axis of the plate) away from the perpendicular to the plate. However, for such a configuration, half of the screw holes may not be suitable for use. In the worse case scenario, none of the holes can be used.

A more recent development in bone fracture fixation disclosed in U.S. 2009/0228010 A1, published Sep. 10, 2009, utilizes a bone fixation system including a bone plate having one or more bi-directional combination holes each of which can accommodate two bone screws, one in each domain of the same hole, one of which is a so-called by-pass screw. hi this type of system, the head of each by-pass screw is cut along a chord to provide a flat extending parallel to the screw shaft which provides clearance for the head of the other screw received in the other domain of the same hole.

While this last system has certain advantages, it also has a drawback in that the by-pass screw must he screwed into one domain of a combination hole in the bone plate so that the flat side of its head faces the other domain of that hole to provide the needed clearance for the second screw being installed in that other domain. In many instances, in order to do this, the by-pass screw may have to be undertightened or overtightened into the underlying bone in order to bring the head fiat in register with the other domain of the same hole, If that screw is undertightened, the bone plate may not be drawn sufficiently to the bone to stabilize the bone fracture. On the other hand, if that screw is overtightened, the screw threads may he stripped from the bone.

Another disadvantage of using bone screws with by-pass heads is that it increases the size of the screw inventory required to he maintained in hospitals, clinics and the like. The use of such screws with by-pass heads also complicates the surgical implantation of the plates in that the surgeon has to be be sure that he is installing the correct screw in each screw hole of the bone plate.

SUMMARY OF THE INVENTION

Accordingly, the present invention aims to provide a bone fixation system consisting of a bone plate and a screw set therefor which addresses the above disadvantages of other such systems.

Another object of the invention is to provide such a system Which optimizes the pullout strength of the plate from a bone to which it is attached.

Yet another object is to provide a bone Fixation system which optimizes the alignment and stabilization of the bone segments in the bone fracture being bridged by the plate.

A further object of the invention is to provide a system of this type whose implantation involves a minimum amount of tissue dissection and retraction.

An additional object of the invention is to provide a bone plate which minimizes the number of different screws required to secure the system's bone plate to a bone.

Still another object of the invention is to provide a method of fixating a bone fracture laving one or more of the above advantages.

Other objects will, in part, be obvious and will, in part, appear hereinafter.

The invention accordingly comprises the several steps and the relation of one or more of such steps with respect to each other, and the device embodying the features of construction, combination of elements and arrangement of parts which are adapted to effect such steps, all as exemplified in the following detailed description, and the scope of the invention will he indicated in the claims.

As used herein, the term "combination hole" or "combination aperture" is meant to refer to a hole or aperture of a bone plate that is configured to accommodate two screws placed in the same hole. That is, each hole has two domains to be described in detail hereinafter, one for each screw.

Also, the term "bi-directional" or "bi-angular" in reference to a combination hole or aperture is meant to refer to a hole or aperture in a bone plate having two domains which accommodate two screws in which the screws are directed at angles from each other and the bone plate, i.e., the directions of the two screws in the same combination hole are nonparallel.

Further, the term "screw" is meant to include a conventional screw having a threaded shank with a threaded (locking) or non-threaded (non-locking) head as well as a peg having a non-threaded shall with a threaded (locking) or non-threaded (non-locking) head.

In view of the foregoing disadvantages inherent in conventional bone fixation systems, the present invention provides a novel system and method for fixating bone fractures, especially long bone fractures. Given that many fractures have not only transverse fracture components but also oblique, or even rather frequently long, fracture lines along the bone, it has been found, advantageous for screw placement, in the case of fracture fixation with a plate, to be directed away from a plane perpendicular to the surface of the plate.

Thus, the present invention provides a bone plate having a bi-angular or bi-directional hole configuration in the form of one or more of such combination holes or apertures, each of which has two non-overlapping domains. One domain of the combination hole may suitably be used to receive a bone screw, e.g., a non-locking conventional screw, extending in one direction away from the perpendicular or even along the perpendicular to the surface of the plate, while the other domain of the same combination hole is suitably used to mate another screw, e.g. as locking screw, in an entirely different non-parallel direction. In use, the locking screw is suitably received in the other domain of the same bi-angular combination hole. The direction of the screw placement per hole depends on the optimal configuration for individual fracture fixation and is not limited as it is in the existing prior art devices.

The full mechanical advantage of the combination bole configuration in accordance with the invention is realized when two screws are mated to the same bi-directional or bi-angular hole. The head of the first screw mated to the plate is suitably positioned to allow the placement in the same combination hole of a second similar or different screw. Having two fixed-angle screws oriented in divergent directions into the substance of the bone enhances the pull out strength of the plate from the bone far beyond that of a single screw oriented perpendicular to the plate. In the preferred embodiment of the invention, the two screws in each combination hole of the bone plate form an inverted A frame configuration which also exhibits excellent anti-torsional characteristics.

It should also be noted that during the surgical act of applying the plate to the fractured bone, critical vessels or nerves, muscle or other soft tissue may be in the way of the path of the intended drill hole in the bone, in accordance with the invention, a surgeon is able to avoid undue retraction on the soft tissue or even to minimize soft tissue dissection by choosing the more suitable direction afforded by the bi-directional hole design in the bone plate. Therefore, an additional benefit of the bi-directional design is its versatility, minimizing the requirement for soft tissue dissection and retraction.

Thus, my bone fixation system includes a bone plate and a specialized screw set. The bone plate has an upper surface and an opposed lower surface which contacts the bone to be fixated. The bone plate includes at least one and usually a plurality of bi-directional divergent combination holes spaced apart along its length.

The central axis of the domains of each combination hole are spaced apart at angles to each other and in reference to the lower plate surface, i.e., the directions of the screws positioned in the two domains of each combination hole are nonparallel. The specialized screw set allows placement of two "full head" screws immediately adjacent in the same combination hole. A full head screw should he understood to be one whose head has a circular cross-section and which has more or less the same circumference as the corresponding domain of the combination hole in which it is placed. That is, the screw head does not have a by-pass or flat. Nor is it otherwise specially shaped or dimensioned to provide clearance for another screw installation in the other domain of the same combination hole.

In some system embodiments, the bone plate may have a suitably serpentine shape to optimize the use of materials around the bi-directional holes and to provide better torsional characteristics. The bi-directional holes may be disposed adjacent, but offset or angled, to one another, e.g., along the length of as bone plate. in other embodiments, the bone plate may have a suitably linear or curved shape. The combination holes may also be placed adjacent to one another, but offset or angled with respect to each other and with respect to the longitudinal axis of the plate. In each case, the central axes of the domains of the combination holes are configured at an angle with respect to each other and with respect to the lower surface of the plate. Also, the bone plate may include both combination and non-combination, i.e. conventional, holes.

The present invention also includes a method of fixating bone factures which includes positioning a bone plate laving a plurality of bi-directional divergent combination holes therethrough to a fracture site in a bone, and inserting full head bone screws through the bi-directional holes of the bone plate into a bone or bone fragments to fixate the fracture, the screws being oriented in the bone in non-parallel directions as described above. Other advantages and a better appreciation of the specific adaptations, variations, and physical attributes of the invention will be gained upon an examination of the following detailed description, taken in conjunction with the accompanying drawings.

DETAILED DESCRIPTION OF ILLUSTRATIVE EMBODIMENTS

Figure 1:
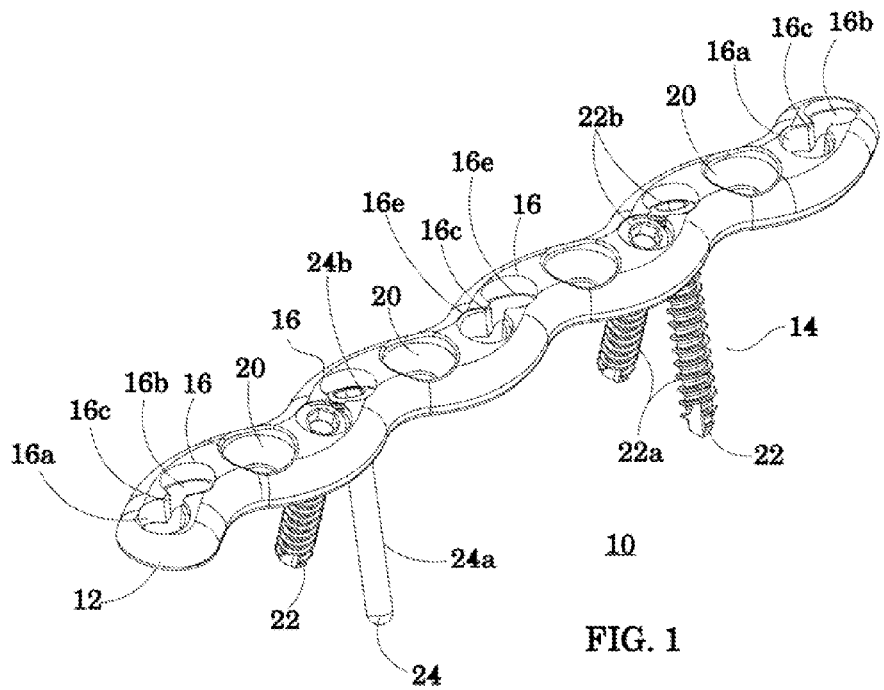
FIG. 1 is a perspective view of a bone fixation system according to the invention incorporating a serpentine bone plate with both single and combination screw holes and a screw set therefor.
Figure 2:
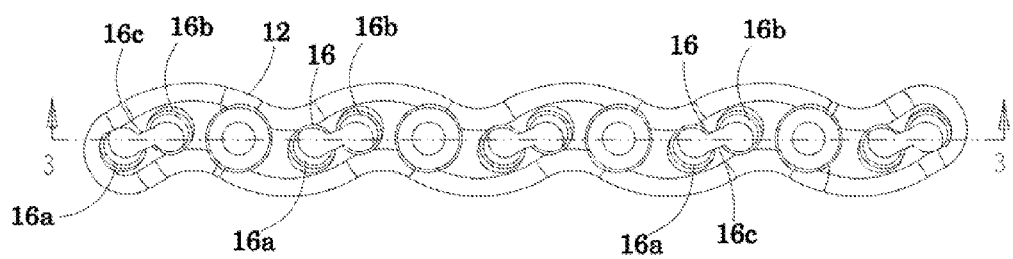
FIG. 2 is a top plan view of the bone plate in the FIG. 1 system.
Figure 3:
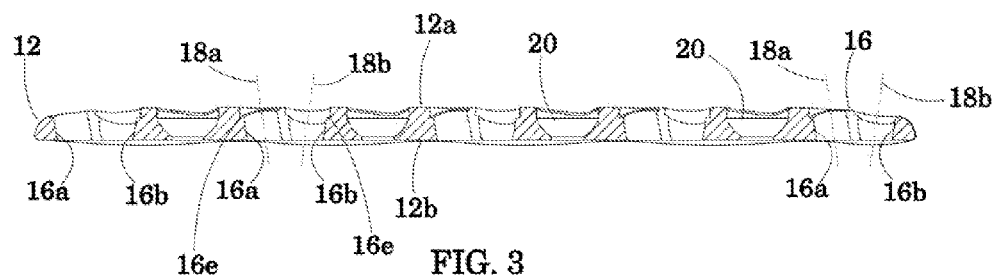
FIG. 3 is a sectional view taken along line 3-3 of FIG. 2.

Referring to FIGS. 1-3 of the drawings, my bone fixation system shown generally at 10 comprises an elongated bone plate 12 made of a suitable rigid biocompatible metal such as titanium or stainless steel and a screw set indicated at 14, of a similar metal, for anchoring the bone plate to the bone to be fixated. The particular dimensions and shape of the bone plate 12 depend upon the size and shape of the bone and the length and dispersion of the bone fracture to he bridged by the plate.

Plate 12 has a first or upper surface 12a and a lower, bone-contacting surface 12b opposite surface 12a. Extending between those surfaces is a lengthwise series of spaced-apart combination holes or apertures 16 disposed along the longitudinal axis of plate 12. Each hole 16 has a predefined shape and size. More particularly, each hole 16 is composed of as pair of substantially circular domains 16a and 16b with a counter-bore 16e and which are offset laterally from one another about the plate axis and may be interconnected by a narrow, relatively short interconnect or neck 16c so that the circumferences of the two domains do not overlap. As in the illustrated system 10, each combination hole 16 has the general shape of a bi-angular, laterally offset figure-eight.

Figures 8, 9:
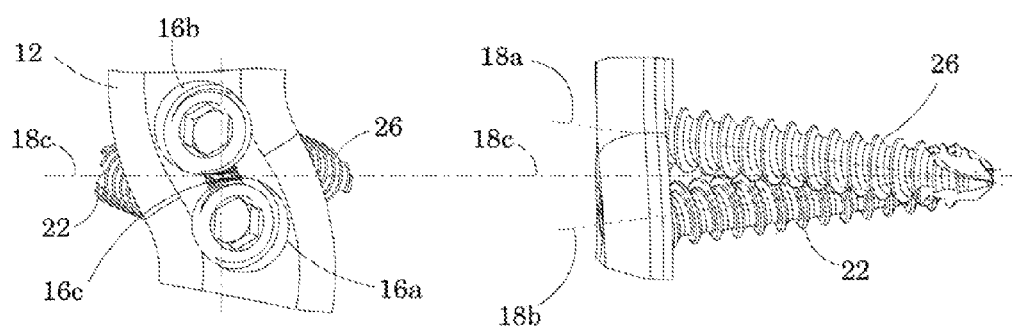
FIG. 8 is a fragmentary top plan view showing the locking screws fully seated in the two domains of the same combination hole of the bone plate.
FIG. 9 is a fragmentary side plan projection view of top plan view in FIG. 8 on the same scale as FIG. 8 showing the locking screws fully seated in the two domains of the same combination hole of the bone plate and converging of the central axis between the combination holes.

In addition to the two domains 16a, 16b of a combination hole 16 being offset laterally, they may also be offset in the longitudinal direction, and convergent as indicated by the domain axes 18a and 18b with a central axis 18c lying perpendicular to the longitudinal axis and equally spaced between 18a and 18b in FIGS. 3, 8, and 9. As illustrated in FIG. 9 the domain axis 18a 18b converge on the central axis 18c at the same latitude. As will be appreciated, the bi-angular offset of the two domains of each combination hole 16 may vary depending upon the particular application.

As indicated above, my system can utilize a bone plate having a variety of shapes. The plate 12 illustrated in FIGS. 1-3 has a serpentine shape. On the other hand, the fixation system 10 shown in FIG. 4 includes a bone plate 12', which is linear. It should be understood that the parts of the different plate embodiments described herein which are in common carry the same identifiers. Also, features in one plate embodiment may be incorporated into the other embodiments. A given bone plate could also he curved along its length, enabling the plate to be anatomically contoured to a particular bone. Alternatively or in addition, the bone plate 12 or 12' may be laterally arched thus allowing the plate to conform to the generally cylindrical surface of the bone to which it will be applied, i.e. the tibia, femur, humerus, full arm bone, etc. Such a plate configuration also allows a conventional bone screw to be inserted obliquely through a hole 16 when a small bone fragment must be gripped and pulled against the plate. Indeed, the bone plate may even be shaped and dimensioned to allow fixation of small bone fragments, e.g. in the hand.

A given bone plate 12, 12' may be provided with any number of combination holes 16 to suit specific surgical applications. The combination holes may be spaced apart evenly along the plate or grouped as needed. Also, the same plate 12, 12' may be provided with other types and configurations of conventional non-combination screw holes between the combination holes 16. For example, the plates 12, 12' depicted in FIGS. 1-4 show conventional spherical screw holes 20 extending perpendicularly through the plates 12, 12'. These non-combination holes 20 may be either threaded or non-threaded.

Figure 5:
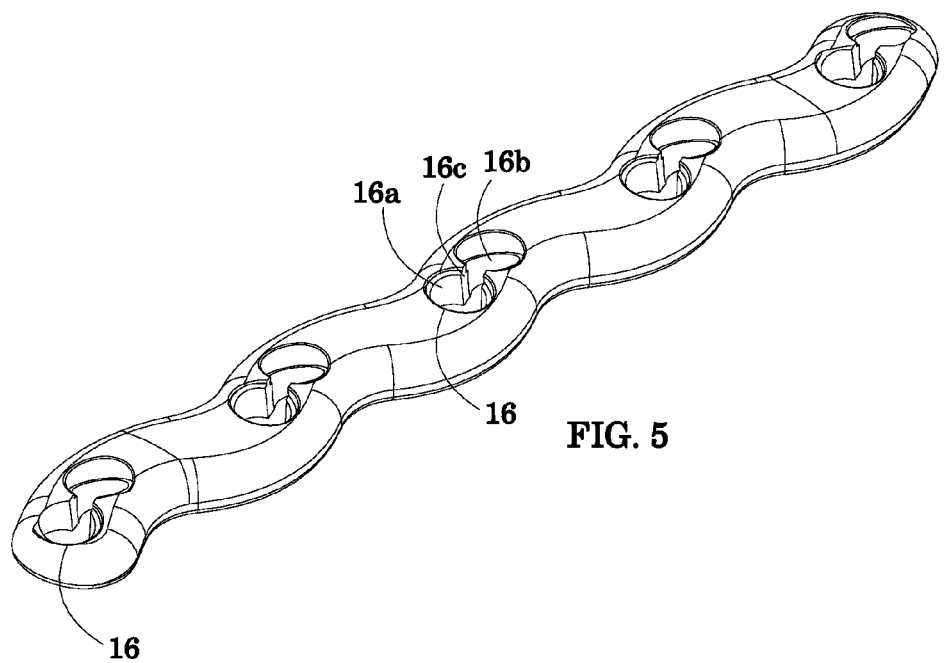
FIGS. 5 and 6 are perspective views showing serpentine and linear bone plates, respectively, having only combination screw holes.
Figure 6:
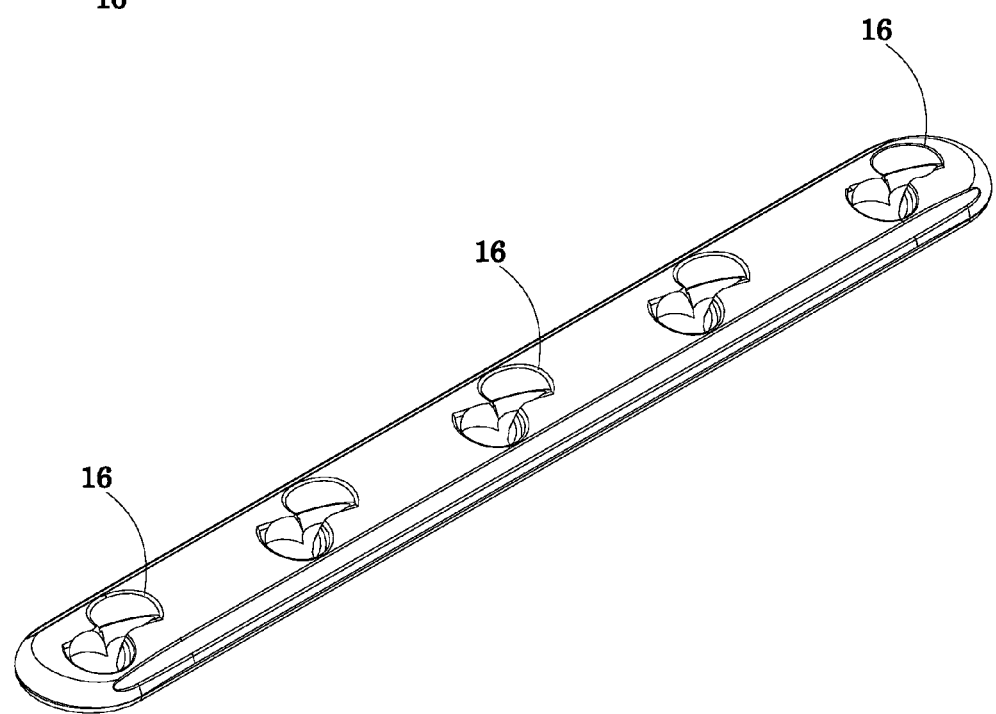

Of course, in other instances, the bone plates 12, 12' may be formed with only bi-directional combination holes 16 as shown in FIGS. 5 and 6.

Still referring to FIGS. 1-4, the screw set 14 component of applicant's system 10 comprises as plurality of full head screws, only some of which are shown in the drawing figures, adapted to be received in some or all of the combination holes 16 in the associated bone plate. Thus, set 14 may include screws 22 having threaded shafts 22a and non-threaded heads 22b, as well as screws 24 with non-threaded shafts 24a and non-threaded heads 24b, i.e. pegs. As noted above, such screws with non-threaded heads are referred to as non-locking screws and are adapted to be received in combination holes 16 having non-threaded domains 16a, 16b.

The screw set 14 may also include so-called locking screws which are full head screws having a threaded head topping a threaded or non-threaded shaft. Such locking screws are shown generally at 26 in FIG. 7. As seen there, each screw 26 has a threaded shaft 26a and a threaded head 26b, the threads 26c of the head 26b being adapted to mesh with the internal threads 28a and 28b of the associated combination hole domains 16a and 16b, respectively.

Figure 4:
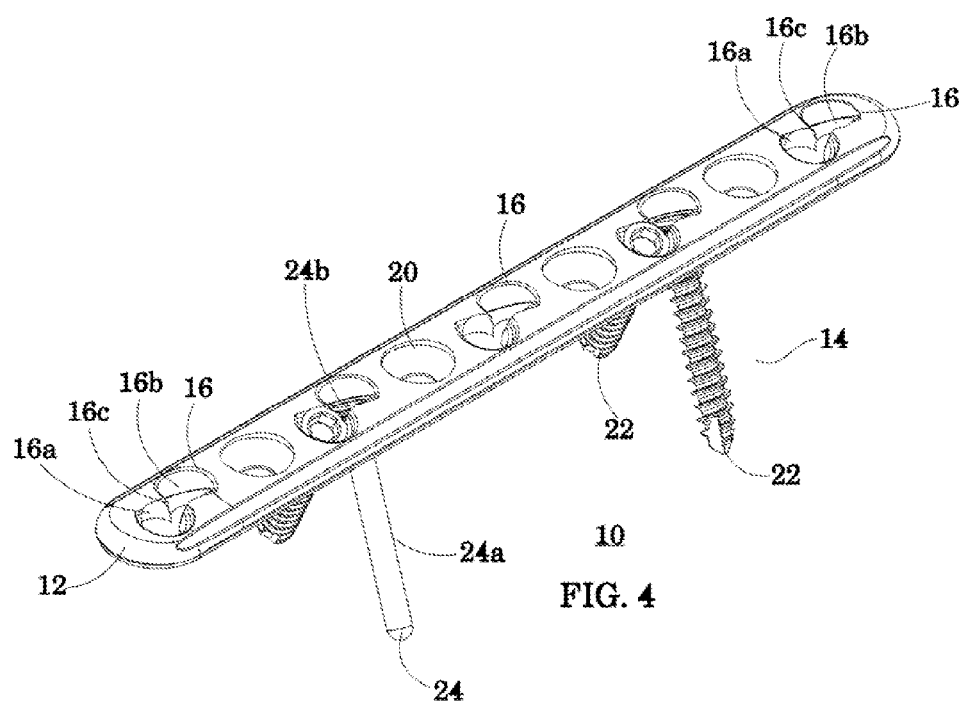
FIG. 4 is a view similar to FIG. 1 of a system whose bone plate has a linear configuration.
Figure 7:
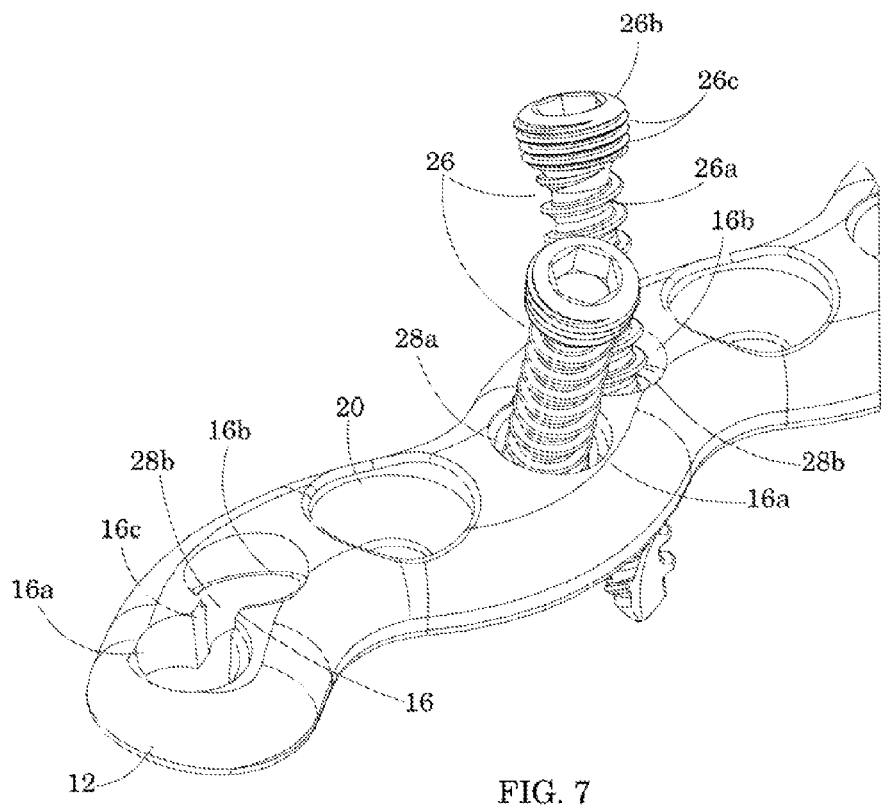
FIG. 7 is a fragmentary exploded perspective view, on a larger scale, of a fixation system showing bone screws in the form of locking screws partially seated in a bidirectional combination hole of a bone plate.

Some plates incorporating this invention may have combination holes both of whose domains are non-threaded as illustrated in FIGS. 1 and 4, while other one plates may have combination holes, both of whose domains are internally threaded, as shown at the right side of FIG. 7. However, it should also he understood that, as shown at the left side of FIG. 7, a given combination hole 16 may have one domain, for example domain 16a, that is non-threaded and another domain, such as domain 16b, which is internally threaded as shown at 18b in that figure. Thus, one of the two full head screws received in the hole 16 of plate 12 in FIG. 7 may he a non-locking screw, such as screw 22 in FIG. 1, received in domain 16a and screwed into the underlying bone to bring the bone to the plate. Another screw, received in domain 16b, may be a locking screw, such as screw 26 in FIG. 7, which is screwed into the bone and whose threaded head is mated to the plate in a locking fashion.

In current known bone fixation systems, a surgeon has to sacrifice several holes in the bone plate to bring the bone to the plate and then use the remaining holes in a "locking mode". In contrast, according to the present invention, no hole is "wasted" and every hole can offer enhanced fixation beyond what existing locking or non-locking screw can provide.

As shown in FIG. 8, to accommodate two full, head screws from the screw set 14 in as single combination hole 16, a non-locking bone screw 22 may be placed in at least one of the domains, 16a or 16b, of plate 12, 12' to provide compression of the fractured bone fragments of the underlying bone. In the other domain, 16b or 16a of the same hole 16, precise spacing of the domains 16a and 16b by interconnect 16c allows a second full head screw, e.g. a locking screw 26, to be accommodated in the other domain of the same combination hole. As described above, the second domain of hole 16 provides an increased angulation for a bone screw with respect to the bone plate and the first screw. Thus, the two divergent screws received in the same bi-angular combination hole provide additional fixation to the underlying bone because the two screws, oriented divergently and converging on a central axis into the bone, offer significantly more resistance to pullout than known existing fixation system configurations. Also, torsional resistance is theoretically increased.

My fixation system with divergent full head screws also provides additional fixation in fractures adjacent to the softer bone proximate to joints, particularly periarticular fractures and those that require articulate subchondras support such as in distal radius fractures, tibial pilon fractures, tibial plateau fractures and the like.

To facilitate their insertion, the screws with threaded shafts can be self-tapping screws or the bone can be predrilled to receive the screws with the aid of a drill guide. Additionally, the screws can he cannulated for insertion of a guide wire to guide screw placement. The hole domains 16a, 16b in the bone plate 12, 12' may have a substantially conical shape for receiving a full head non-locking screw or be provided with a doublelead thread for a locking screw. Also, the lengths of the individual screw shafts may be selected for a particular application and may have rounded, diamond or trocar-shaped tips.

In accordance with my bone fixation method, a bone plate having along its length a plurality of bi-directional combination holes therethrough may he positioned at a fracture site on a bone. Full bead bone screws are then inserted through the combination holes of the bone plate into the bone or bone fragments to draw the bone against the plate to fixate the fracture, the bone screws being oriented in the bone in non-parallel directions.

It should be noted that during the surgical act of securing the plate to the fractured bone using the bone screws, critical vessels, nerves or muscle or other soft tissue or bone may be in the way of the path of the intended screw hole in the bone. In accordance with this invention, a surgeon is able to avoid undue retraction of the soft tissue in the bone and to minimize soft tissue dissection by choosing a more suitable screw direction that is afforded by the bi-directional combination hole design of the bone plate. Therefore, an additional benefit of this design is its versatility which results in the minimizing of the requirement for soft tissue dissection and retraction.

In summary, the full mechanical advantage of the combination hole configuration in accordance with this invention is realized when two full head screws are mated to the same bi-directional combination hole in a bone plate such that the two screws are oriented in divergent directions and converging on a central axis into the substance of the bone, thereby enhancing the pullout strength of the plate from the bone far beyond that which can be achieved by single screws oriented perpendicular to the plate.

The foregoing description is considered as illustrative only of the principles manifested in the embodiments of the invention. Since numerous modifications and changes may readily occur to those skilled in the art, it is not desired to limit the invention to the exact construction and operation shown and described above. Accordingly, all suitable modifications and equivalents ate considered to be within the scope of the invention.

It also to be understood that the following claims are intended to cover all of the generic and specific features of the invention described herein.

The invention claimed is:

1. A bone plate comprising:
an elongated member having a longitudinal axis. an upper surface, a lower surface, and one or more bi-directional combination holes extending from the upper surface to the lower surface, each hole consisting of a pair of substantially circular divergent domains with non-overlapping circumferences and an interconnect which separates the circumferences of the two domains, each domain having a counterbore, said domains being configured and dimensioned to receive a pair of full head bone screws being in all-around circumferential contact with said domains for anchoring into a bone or fragments thereof, each domain comprises a central longitudinal axis, each hole comprises a transverse axis extending perpendicular to said longitudinal axis of said elongated member and through said interconnect, wherein said central longitudinal axes of each domain diverge relative to each other while converging towards said transverse axis in a direction away from said lower surface of said bone plate.

2. The bone plate described in claim 1 wherein the bone plate is straight.

3. The bone plate defined in claim 1 wherein the bone plate having a compound curve whose central curve is convex and serpentine.

4. The bone plate defined in claim 1 wherein the lower surface of the bone plate is flat.

5. The bone plate defined in claim 1 wherein the lower surface of the bone plate has an arched cross-section.

6. The bone plate defined in claim 1 wherein at least one of said combination holes has domains with non-threaded walls.

7. The bone plate defined in claim 1 wherein at least one of said combination holes has domains with threaded walls.

8. The bone plate defined in claim 1 wherein at least one of said combination holes has one domain with a non-threaded wall and a second domain with a threaded wall.

9. The bone plate defined in claim 1 wherein said one or more holes is shaped like a bi-angular, laterally offset figure eight.

10. The bone plate of claim 1, wherein said bi-directional combination holes comprise a doublelead thread.

11. A bone plate assembly comprising the bone plate defined in claim 1, and a pair of full head bone screws received in one of said holes so that the heads thereof are in all-around contact with different domains of said one of the holes.

12. A bone plate comprising:
an elongated member having a longitudinal axis, an upper surface, and a lower surface;
one or more bi-directional combination holes extending through said elongated member from the upper surface to the lower surface, each hole defines a longitudinal axis that is angled with respect to the longitudinal axis of the elongated member and each hole defines a bisecting axis that is perpendicular to said longitudinal axis of said elongated member, each hole consists of a pair of substantially circular divergent domains, each domain defines a central axis, wherein said central axis of each domain diverges relative to one another and converges towards said bisecting axis in a direction away from said lower surface of said bone plate, said hole defines a third axis perpendicular to said bisecting axis and said longitudinal axis of said elongated member, wherein said central axis of each domain cross said bisecting axis below said lower surface at a common depth defined along said third axis, said domains being configured and dimensioned to receive a pair of full head bone screws being in all-around circumferential contact with said domains for anchoring into a bone or fragments thereof.

13. The bone plate of claim 12, wherein said two domains being offset laterally and offset in a direction along said longitudinal axis of said elongated member.

14. The bone plate of claim 12, wherein said bi-directional combination holes are angled with respect to each other and with respect to said longitudinal axis of said elongated member.

15. The bone plate of claim 12, wherein said bi-directional combination holes are configured to receive screws resulting in an inverted A frame configuration.

16. The bone plate of claim 12, wherein said bi-directional combination holes comprise a doublelead thread.

17. A bone plate with a bi-directional combination hole system comprising:
a bone plate having an elongated member with a longitudinal central axis, having an upper surface and a lower surface, and one or more bi-directional combination holes; said bi-directional combination holes having a first hole having a first domain laterally offset and parallel to said longitudinal central axis of said plate; said bi-directional combination holes having a second hole having a second domain laterally offset and parallel to said longitudinal central axis of said plate, wherein said second hole is laterally opposite said first hole and longitudinally offset from said first hole; said first domain and second domain each having a center axis; said center axis of said first domain diverging relative to said center axis of said second domain; said bi-directional combination holes defining a common central plane which bisects each hole and is equally spaced between said first and second domains and perpendicular to said longitudinal central axis of said plate; said first domain and second domain center axis each converge on said common central plane; said first domain and second domain center axis each converge on said common central plane at a same depth located below the lower surface of said plate; said first domain and second domain each define a circumference, wherein said circumferences do not overlap with one another; said first domain and second domain having a counterbore; said first domain and second domain are configured to join in a direct mating relationship with a full head bone screw such that the heads thereof are in all-around contact with each domain.

18. The bone plate of claim 17, wherein said bi-directional combination holes include a doublelead thread.

19. A method of bone fixation wherein the method comprises:
providing a bone plate comprising:
an elongated member having a longitudinal axis. an upper surface, a lower surface, and one or more bi-directional combination holes extending from the upper surface to the lower surface, each hole consisting of a pair of substantially circular divergent domains with non-overlapping circumferences and an interconnect which separates the circumferences of the two domains, each domain having a counterbore, said domains being configured and dimensioned to receive a pair of full head bone screws being in all-around circumferential contact with said domains for anchoring into a bone or fragments thereof, each domain comprises a central longitudinal axis, each hole comprises a transverse axis extending perpendicular to said longitudinal axis of said elongated member and through said interconnect, wherein said central longitudinal axes of each domain diverge relative to each other while converging towards said transverse axis in a direction away from said lower surface of said bone plate;
providing a plurality of full head bone screws;
positioning said bone plate at a fracture site on a bone;
inserting said full head bone screws through said combination holes of said bone plate into a bone or bone fragment to draw said bone against said plate to fixate said fracture site on said bone, wherein said bone screws are oriented in said bone in non-parallel directions relative to one another.

* * * * *